US00RE39923E

(19) United States
(12) Reissued Patent
Blom

(10) Patent Number: US RE39,923 E
(45) Date of Reissued Patent: Nov. 20, 2007

(54) FLANGED CYLINDRICAL IMPLANT AND METHOD OF INSERTION

(75) Inventor: Eric D. Blom, Carmel, IN (US)

(73) Assignee: Hansa Medical Products, Inc., Indianapolis, IN (US)

(21) Appl. No.: 08/393,185
(22) Filed: Feb. 23, 1995

Related U.S. Patent Documents

Reissue of:
(64) Patent No.: 5,300,119
Issued: Apr. 5, 1994
Appl. No.: 07/818,853
Filed: Jan. 10, 1992

(51) Int. Cl.
*A61F 2/20* (2006.01)

(52) U.S. Cl. ..... 623/9; 623/14.11; 623/23.64; 128/207.29; 128/207.14; 128/887; 600/29

(58) Field of Classification Search ..... 623/9, 623/14.11, 23.64, 23.75; 128/207.29, 207.14, 128/887, 885, DIG. 25; 600/29, 30, 32
See application file for complete search history.

(56) References Cited

U.S. PATENT DOCUMENTS 4,246,897 A * 1/1981 Muto ..... 128/207.15
4,291,690 A * 9/1981 Jessen ..... 128/207.29
4,435,853 A * 3/1984 Blom et al. ..... 623/9

(Continued)

FOREIGN PATENT DOCUMENTS

DE 3121976 * 3/1982
WO WO 88/02238 * 4/1988

OTHER PUBLICATIONS

K. Nabeya–K. Onozawa and S. Ri, "Brushing Cytology with Capsule for Esophageal Cancer", Kyorin University School of Medicine, Chir Gastroent (Surg Gastroent). vol. 13, No. 2, pp. 101–107, 1979.

Pellanda et al., "Abrasive Esophageal Cytology for the Oncological Follow–up of Patients With Head and Neck Cancer", The Laryngoscope, Oct. 1999, pp. 1703–1708.

(Continued)

*Primary Examiner*—Paul B. Prebilic
(74) *Attorney, Agent, or Firm*—Barnes & Thornburg LLP

(57) ABSTRACT

[A device for insertion into a puncture in a tracheoesophageal wall includes a cylindrical body and a flexible first flange provided on an outside surface of the body. The flange has a use orientation in which it projects generally outwardly from the outside surface of the body and an insertion orientation in which it is resiliently folded toward the axis of the body. A retainer constructed of a material soluble in fluids present in the tracheoesophageal wall and esophagus retains the flange in its resiliently folded orientation. A method for inserting the device into the puncture comprises the steps of resiliently deflecting the flange toward the axis of the body, placing the retainer over the resiliently folded flange, and either pushing the body, resiliently folded flange first, into the puncture so that the resiliently folded flange lies on the esophageal side of the tracheoesophageal wall, or pulling the body, resiliently folded flange first, into the puncture so that the resiliently folded flange lies on the tracheal side of the tracheoesophageal wall.] *A device for insertion into an opening in a wall in a human body includes a cylindrical device body having a longitudinal axis and a flexible first flange provided on an outside surface of the device body. The flange has a use orientation in which it projects generally outwardly from the outside surface of the device body and an insertion orientation in which it is resiliently folded toward the axis of the device body. A retainer retains the flange in its resiliently folded orientation. The retainer is constructed of a material soluble in fluids present adjacent the wall. A method for inserting the device into the opening comprises resiliently deflecting the flange toward the axis of the device body and placing over the resiliently folded flange a retainer of a material soluble in fluids present adjacent the wall.*

16 Claims, 6 Drawing Sheets

U.S. PATENT DOCUMENTS 4,596,579 A * 6/1986 Pruitt ..... 623/9
4,614,516 A * 9/1986 Blom et al. ..... 623/9
4,623,348 A * 11/1986 Feit ..... 604/264
4,653,660 A * 3/1987 Shaw ..... 220/86.2
4,695,275 A * 9/1987 Bruce et al. ..... 606/264
4,911,716 A * 3/1990 Blom et al. ..... 623/9
4,964,850 A * 10/1990 Bouton et al. ..... 604/54
5,078,743 A * 1/1992 Mikalov et al. ..... 623/9
5,090,420 A * 2/1992 Nielsen ..... 600/577
5,246,455 A * 9/1993 Shikani ..... 623/10
5,919,231 A * 7/1999 Blom et al. ..... 623/9

OTHER PUBLICATIONS

Roth, et al, "Cytologic Detection of Esophageal Squamous Cell Carcinoma and Precursor Lesions Using Balloon and Sponge Samplers in Asymptomatic Adults in Linxian, China", 1997 American Cancer Society, pp. 2047–2059.

* cited by examiner

FLANGED CYLINDRICAL IMPLANT AND METHOD OF INSERTION

Matter enclosed in heavy brackets [ ] appears in the original patent but forms no part of this reissue specification; matter printed in italics indicates the additions made by reissue.

This invention relates to a method and apparatus for the delivery, or placement, of, for example, a voice prosthesis device into a puncture provided in the tracheoesophageal wall of a speech restoration patient.

A speech restoration technique is known wherein air from the trachea is diverted from its normal flow path out through the tracheostoma to a flow path through a voice prosthesis providing a more or less permanent passageway to the esophagus. Esophageal speech results. See U.S. Pat. Nos. 4,435,853; 4,614,516; and 4,911,716. Voice prostheses currently in use for providing controlled air pathways through tracheoesophageal punctures incorporate flexible retention collars. The retention collar lies against the esophageal surface of the tracheoesophageal wall to reduce the likelihood of dislodgement of the prosthesis from the puncture. While this configuration substantially improves retention, the presence of the large retention collar makes insertion of a prosthesis more difficult and traumatic to the tissue surrounding the tracheoesophageal puncture. A possibility inherent in difficult or traumatic prosthesis insertion is incomplete insertion. Incomplete insertion may result in aspiration of the prosthesis into the airway. The prosthesis may be expelled by coughing, requiring endoscopic retrieval from the airway. Additionally, concern about prosthesis insertion difficulty may prevent some patients and physicians from employing this method of voice restoration.

According to an aspect of the invention, a retainer is provided for atraumatic insertion of a prosthesis into a puncture in the tracheoesophageal wall. The prosthesis includes a cylindrical body and a flexible first flange provided on an outside surface of the body. The flange has a use orientation in which it projects generally outwardly from the outside surface of the body and an insertion orientation in which it is resiliently folded toward the axis of the body. The retainer retains the flange in its resiliently folded orientation.

The retainer illustratively is constructed of a material soluble in fluids present in the tracheoesophageal wall and the esophagus.

Illustratively, the first flange is positioned adjacent a first end of the body which is inserted through the puncture.

Additionally, illustratively, the prosthesis further comprises a second flange spaced along the body from the first flange toward a second end of the body. Illustratively, the second flange is also a flexible flange.

According to another aspect of the invention, a method is provided for atraumatically inserting into a puncture in the tracheoesophageal wall a prosthesis including a cylindrical body and a flexible flange provided on an outside surface of the body. The flange has a use orientation in which it projects generally outwardly from the outside surface of the body. The method comprises the steps of resiliently deflecting the flange toward the axis of the body and placing over the resiliently folded flange a retainer.

Illustratively the retainer is constructed of a material soluble in fluids present in the tracheoesophageal wall and the esophagus.

Illustratively, the method further comprises the step of pushing the body, resiliently folded flange first, into the puncture so that the resiliently folded flange lies on the esophageal side of the tracheoesophageal wall.

Alternatively, the method further comprises the step of pulling the body, resiliently folded flange first, into the puncture so that the resiliently folded flange lies on the tracheal side of the tracheoesophageal wall.

The term "cylindrical body", as used herein, means a body including a surface generated by a straight line moving always parallel to another straight line in a closed path.

The invention may best be understood by referring to the following detailed description and accompanying drawings which illustrate the invention. In the drawings.

Figure 2:
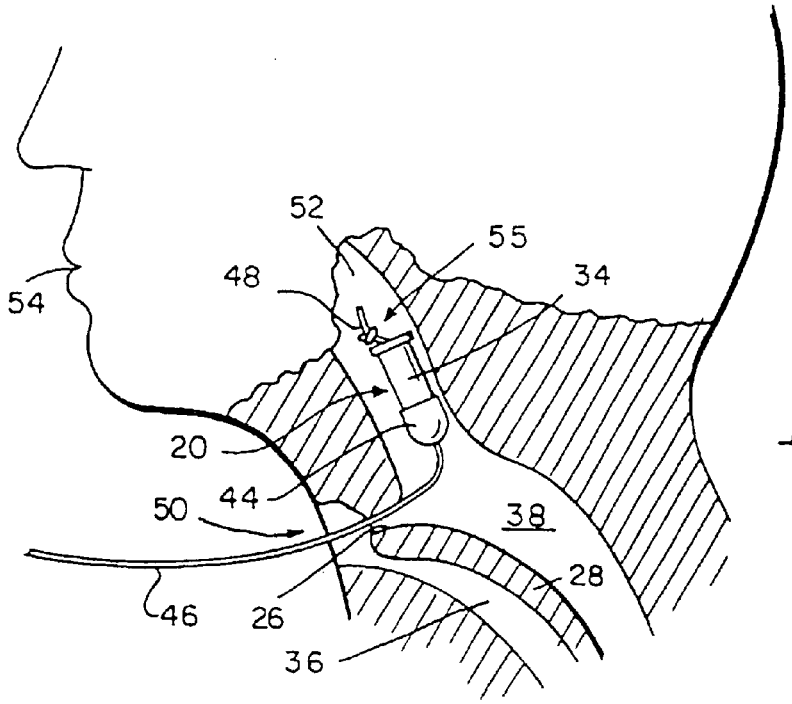
FIG. 2 illustrates a step in a method of insertion of the voice prosthesis device of FIG. 1 according to the invention.

Turning now to the drawings, a voice prosthesis device 20 includes a body 22 of a pliable silicone. The silicone must be rigid enough to withstand the forces placed upon it by the wall 24 of the puncture 26 through the tracheoesophageal wall 28 in which it resides. It must also be pliable enough to permit the folding of the retention flanges 30, 32 formed on its outside surface 34 adjacent its tracheal 36 and esophageal 38 ends, respectively. Flanges 30, 32 are responsible for positioning body 22 in the puncture 26 and reducing the likelihood of it being displaced in either the tracheal 36 or esophageal 38 direction.

Figure 3:
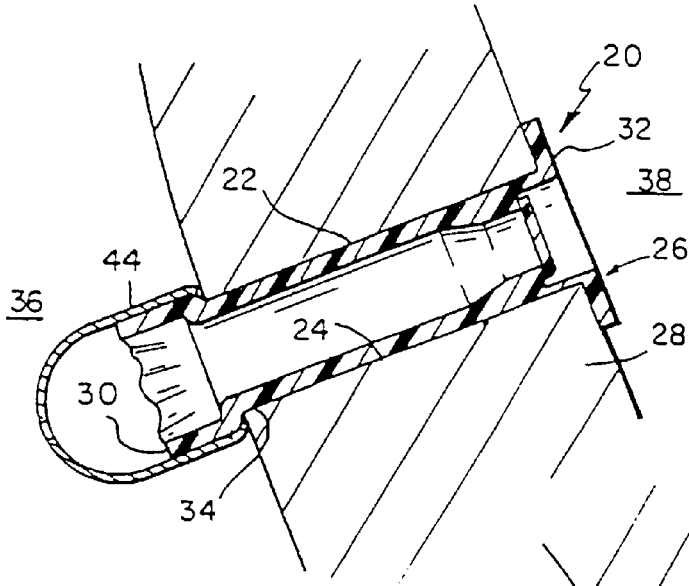
FIG. 3 illustrates a further step in the method, a step of which is illustrated in FIG. 2.
Figure 1:
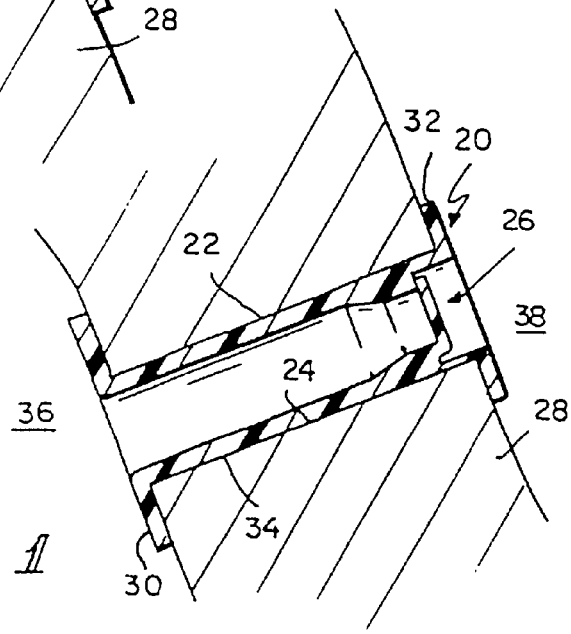
FIG. 1 illustrates a fragmentary sectional view through the tracheoesophageal wall of a wearer of a voice prosthesis device according to the present invention and longitudinally through the voice prosthesis device itself.
Figure 6:
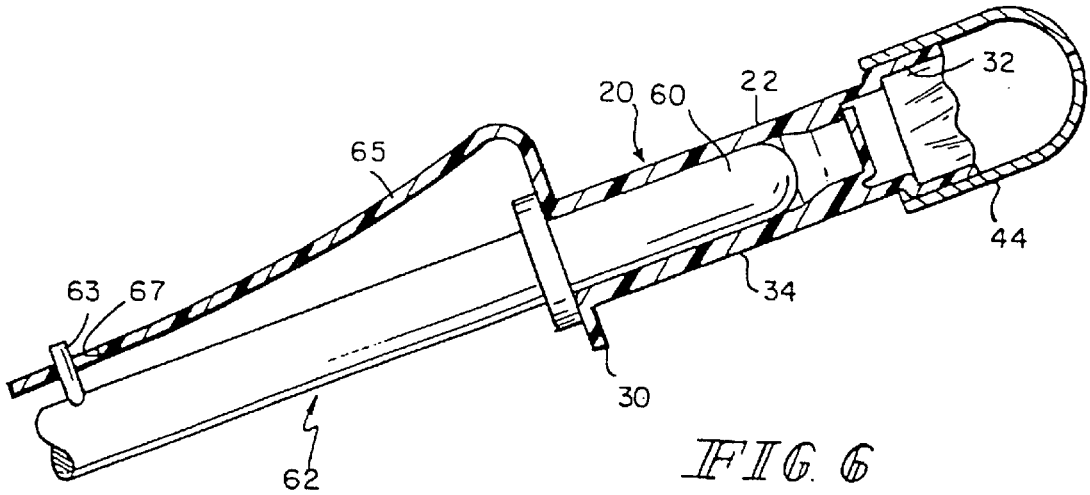
FIG. 6 illustrates a step in a method of insertion of the voice prosthesis device of FIG. 1 according to the invention.
Figure 7:
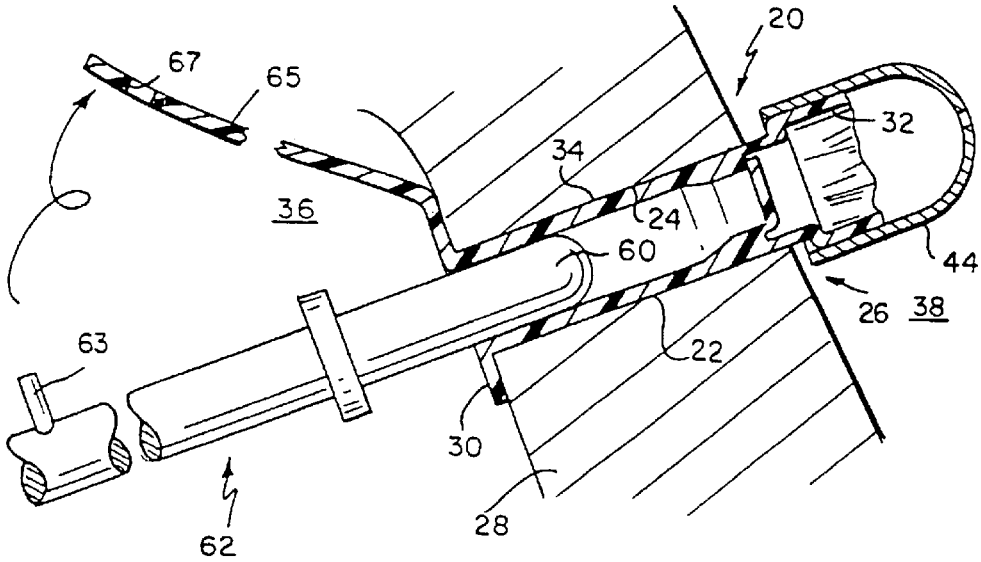
FIG. 7 illustrates a step in a method of insertion of the voice prosthesis device of FIG. 1 according to the invention.

Flanges 30, 32 are sufficiently flexible that they can be collapsed or folded into non-use, or insertion, orientations as illustrated by flange 30 in FIGS. 2–3 and flange 32 in FIGS. 6–7. Flanges 30, 32 are retained in these orientations by retainer 44 which illustratively may be cut-off portions of gelatin capsules. Once the voice prosthesis device 20 is inserted into the puncture 26, fluids such as saliva and the like, present in the tracheoesophageal wall 28 and the esophagus 38 dissolve the retainers 44 permitting the flanges 30, 32 to assume their use orientations illustrated in FIG. 1.

FIGS. 2 and 3 illustrate one method of delivery of a voice prosthesis 20 into a puncture 26. In this method, a pediatric catheter 46 (approximately French size 4), preferably, with a Cudé tip, is threaded through the tracheostoma 50, puncture 26 and upward through the pharynx 52 and out through the mouth 54 of a patient. The voice prosthesis 20 with flange 30 captured by a retainer 44 in folded, or insertion, orientation, is then threaded onto the tip 48 of the catheter 46. The retainer 44 is provided with a hole 53 in the tip thereof through which catheter 46 is threaded. A knot 55 is tied in the tip 48 of the catheter 46 to capture prosthesis 20 thereon, and the catheter 46 is pulled back downward through the pharynx 52 and puncture 26. This properly locates voice prosthesis 20 with flange 32 in its deployed, use, orientation and flange 30 still captured in its folded, non-use orientation. However, as retainer 44 is exposed to secretions and the like in the esophagus 38 and tracheoesophageal wall 28, retainer 44 dissolves and flange 30 deploys to its use orientation, positioning prosthesis 20 in puncture 26. Of course, catheter 46 may be removed at any time once voice prosthesis 20 is in place in the puncture, but the clinician may choose to wait to remove catheter 46 until flange 30 is deployed. The catheter 46 is removed by threading it back up through the pharynx 52, out through the mouth 54, untying the knot 55, and then pulling the catheter 46 out through the tracheostoma 50.

Figure 5:
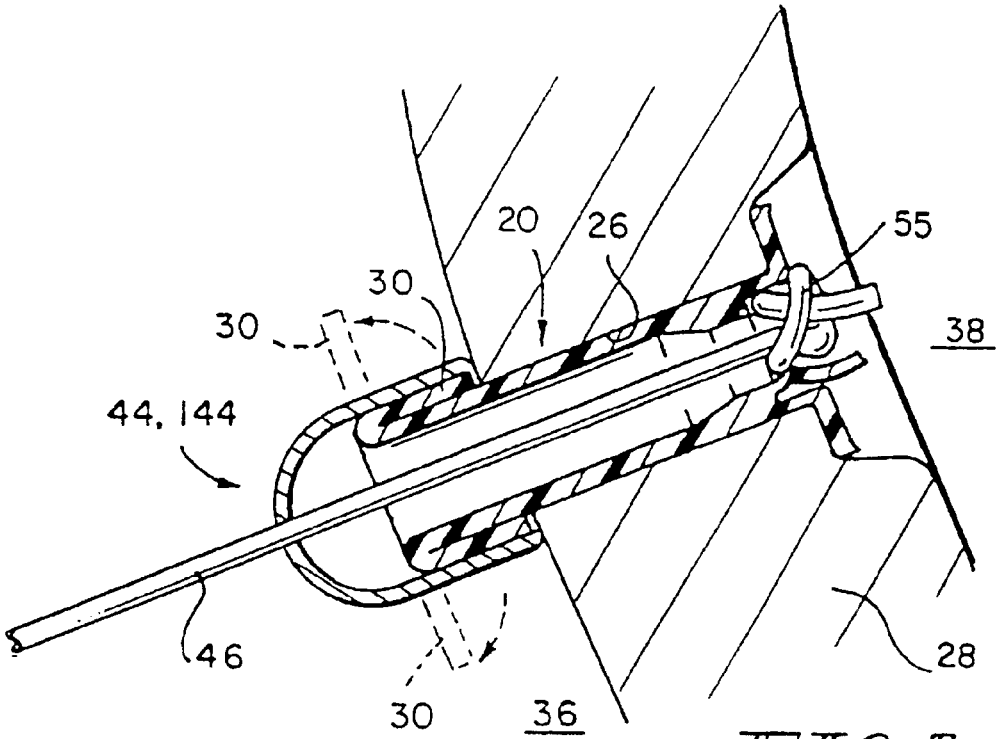
FIG. 5 illustrates a step in another method of insertion of the voice prosthesis device of FIG. 1 according to the invention.
Figure 4:
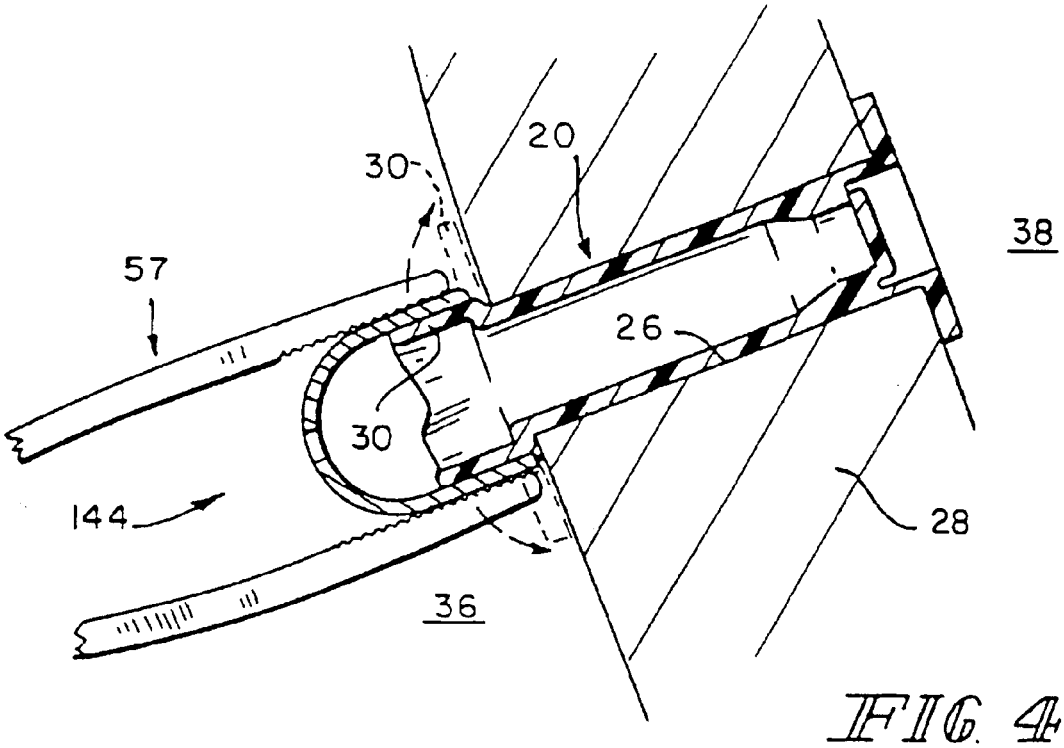
FIG. 4 illustrates a step in another method of insertion of the voice prosthesis device of FIG. 1 according to the invention.

Steps in two more insertion techniques are illustrated in FIGS. 4–5. In these techniques, a retainer 144 is employed which may or may not be soluble in fluids present in the tracheoesophageal wall and the esophagus. These methods work equally well in both cases. In these methods, the retainer 144 is placed over flange 30 to capture it in either forward folded (FIG. 4) or rearward folded (FIG. 5) orientation. The catheter 46 is located as in the embodiment of FIGS. 2–3 and the prosthesis 20 with retainer 144 thereon is threaded onto the catheter 46 and secured. The prosthesis is pulled downward through the pharynx 52 and located in the puncture 26. As illustrated in FIG. 4, the clinician then threads the catheter back up through the pharynx 52, unties the knot 55, and pulls the catheter 46 out. Finally, the clinician inserts a forceps, tweezers or the like 57 through the tracheostoma 50, removes the retainer 144 and pulls it out, deploying the flange 30 to its broken line position illustrated in FIG. 4.

A step in another technique for deploying flange 30 is illustrated in FIG. 5. In FIG. 5, flange 30 has been deflected rearwardly during the process of placing a retainer 44 or 144 on the leading end of prosthesis 20. As in the embodiment illustrated in FIG. 4, the catheter 46 is located as in the embodiment of FIGS. 2–3 and the prosthesis 20 with retainer 44 or 144 thereon is threaded onto the catheter 46 and secured. The prosthesis is then pulled downward through the pharynx 52 and into the puncture 26. However, instead of simply locating the prosthesis 20 correctly in the puncture 26, tension is maintained on catheter 46 sufficient to deflect the esophageal side 38 of the tracheoesophageal wall 28 toward the tracheal side 36 thereof. Then the retainer 44 is permitted to dissolve or the retainer 144 is removed as described in connection with FIG. 4, deploying flange 30 to its broken line orientation. Then the tension on catheter 46 is released, permitting prosthesis 20 to assume its proper orientation in puncture 26 and catheter 46 is removed, for example as described in connection with FIG. 4.

FIGS. 6 and 7 illustrate another method of delivery of a voice prosthesis 20 into a puncture 26. In this method, a retainer 44 is placed over flange 32, folding flange 32 into its non-use, or insertion, orientation. The voice prosthesis 20 is placed on the tip 60 of an insertion tool 62. Insertion tool 62 has a retainer peg 63. Voice prosthesis device 20 is provided with a strap 65 at its tracheal 36 end, illustratively formed on flange 30. Strap 65 is provided with an aperture 67 for accommodating peg 63 to retain prosthesis device 20 on tool 62 during insertion of device 20. Tool 62 is then manipulated through the tracheostoma (such as tracheostoma 50 in FIG. 2) of the wearer, and voice prosthesis 20 is inserted through the puncture 26. This properly locates voice prosthesis 20 with flange 30 in its deployed, or use, orientation and flange 32 still captured in its folded, non-use, orientation. However, as retainer 44 is exposed to saliva and the like on the esophageal 38 side of tracheoesophageal wall 28, retainer 44 dissolves and flange 32 deploys to its use orientation, positioning prosthesis 20 in puncture 26. Of course, tool 62 may be removed from prosthesis 20 at any time by removing strap 65 from peg 63, and then withdrawing tool 62. However, again, the clinician may choose to wait to remove tool 62 until flange 32 is deployed. Finally, since strap 65 is not needed once prosthesis 20 is inserted, strap 65 can be clipped from flange 30 and discarded.

Figure 8:
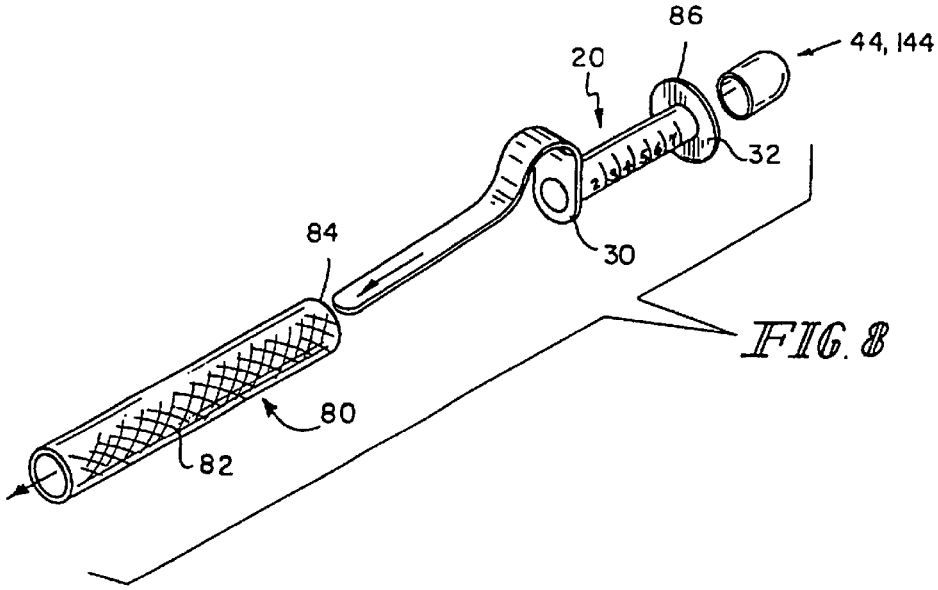
FIGS. 8, 9 and 10 illustrate steps in a method of placement of a retainer onto a speech prosthesis according to the present invention.
Figure 9:
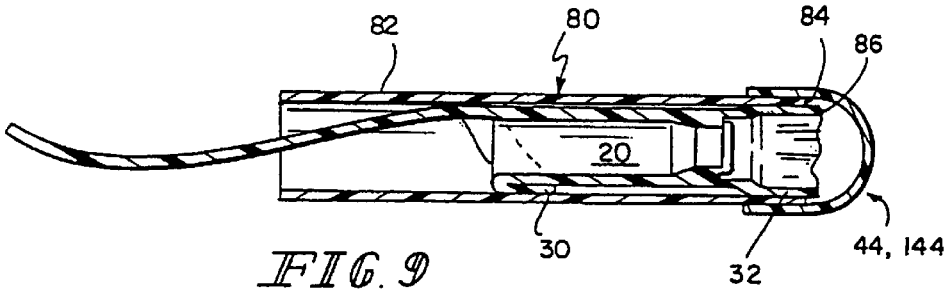
Figure 10:
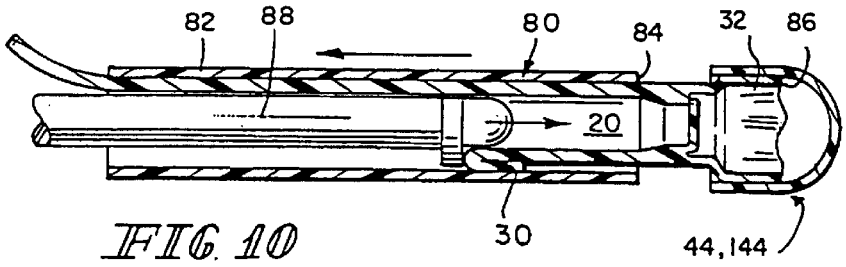

FIGS. 8–10 illustrate steps in the loading of a flange, whether it be flange 30 or 32, into a retainer 44 or 144, to the orientation illustrated in FIGS. 2–4, 6 and 7. In the first step in the method, illustrated in FIG. 8, the prosthesis 20 is inserted into a thin-walled tube 80 to the orientation illustrated in FIG. 9. The outer sidewall 82 of tube 80 illustratively is knurled or otherwise textured to aid in gripping of the tube 80 during the process. Once the prosthesis has reached the orientation illustrated in FIG. 9, the retainer 44 or 144 is placed over the end 84 of the tube 80 from which the edge 86 of the folded flange 30 or 32 projects slightly. Then, referring to FIG. 10, a tool 88 of somewhat the same general configuration as tool 62 is pushed through the open end of the tube 80, engages the open end of prosthesis 20 and pushes prosthesis 20 out of the tube 80 carrying the retainer 44 or 144 with it to retain flange 30 or 32 in its folded orientation illustrated in FIGS. 2–4, 6–7, 9 or 10. The prosthesis 20 is then ready for insertion using one of the methods described in connection with FIGS. 2–4 and 6–7. To load a flange 30 or 32 to the orientation illustrated in FIG. 5, the retainer 44 or 144 is simply pushed on an end of the prosthesis 20 deflecting the flange 30 or 32 along the length of prosthesis 20.

Figure 11:
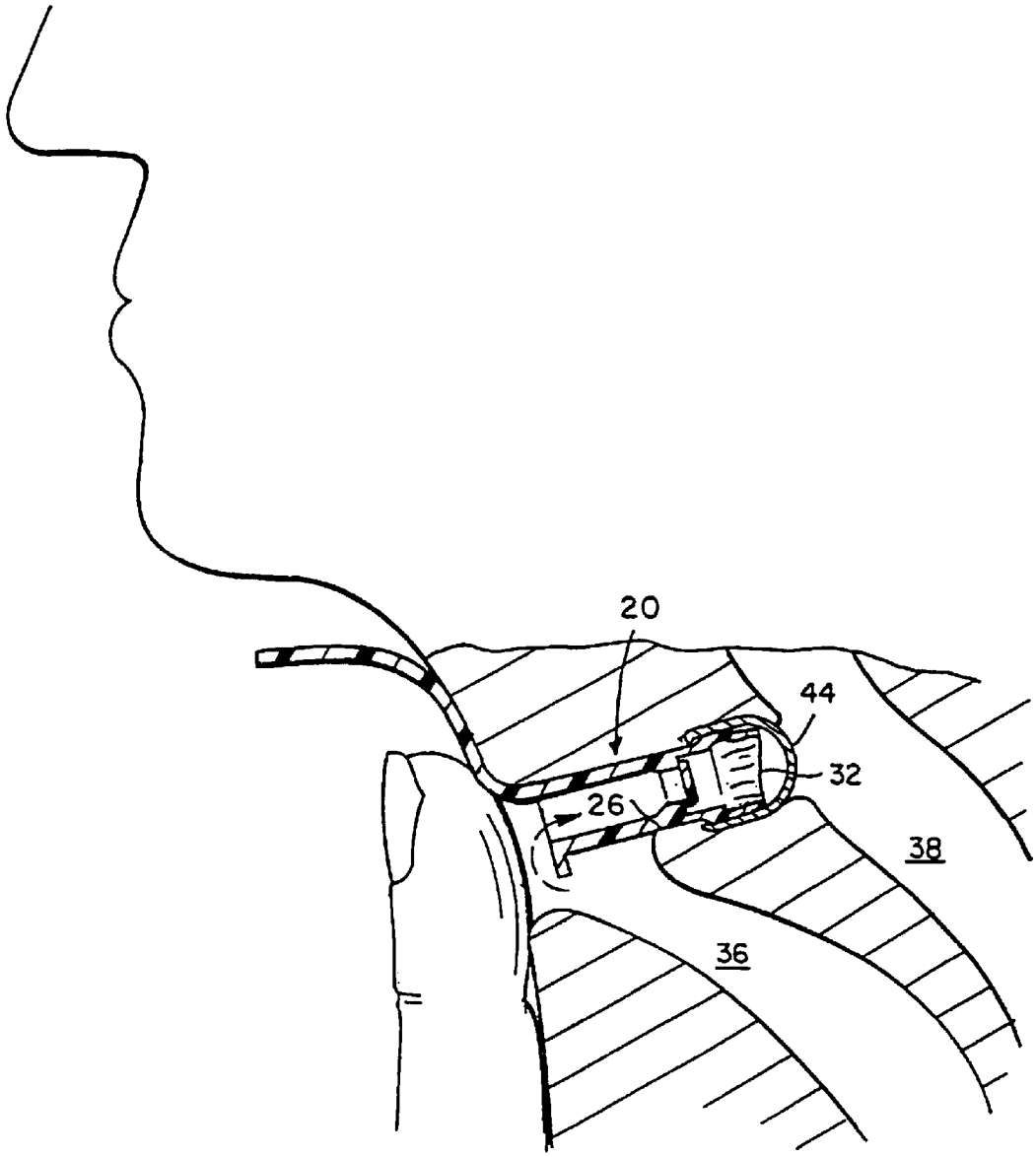
FIG. 11 illustrates a method for checking the placement of a speech prosthesis according to the present invention.

It is to be noted that if the insertion method, a step of which is described in connection with FIGS. 6–7 is employed, one test for proper deployment of the flange 32 is illustrated in FIG. 11. Namely, if the patient attempts to initiate esophageal speech through prosthesis 20 and too much force is required to get airflow through the prosthesis 20, that is an indication of incomplete deployment of the flange 32. This may mean that dissolution of the retainer 44 is incomplete and/or that the prosthesis 20 is too short to extend all the way through the puncture 26 from the tracheal end 36 to the esophageal end 38 thereof. This provides a convenient technique for use with the measuring probe which is used to measure the length of the puncture 26 between the trachea 36 and esophagus 38 to determine the correct length of prosthesis 20 for the patient.

Figure 12:
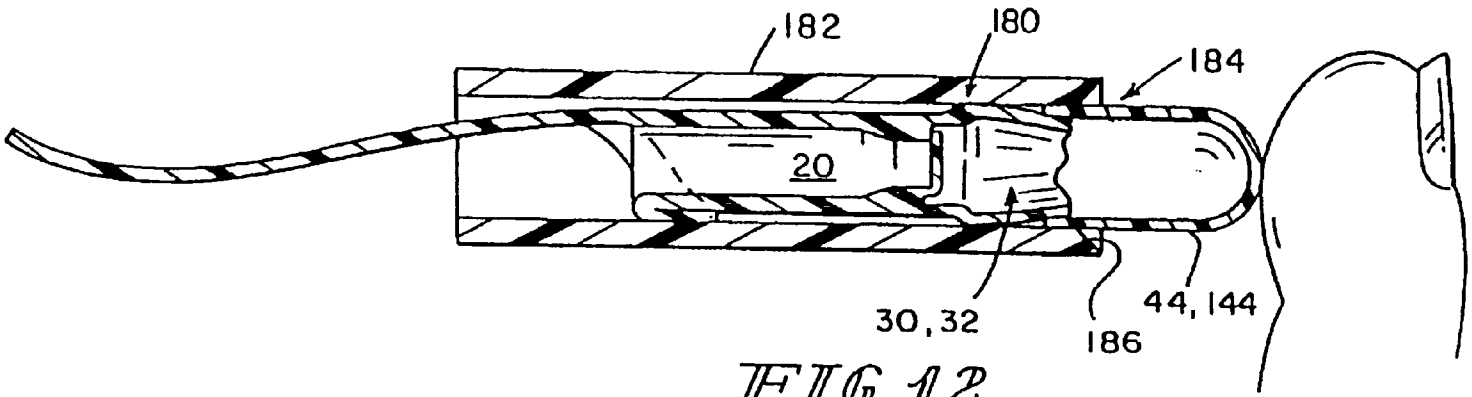
FIG. 12–13 illustrate steps in a method of placement of a retainer onto a speech prosthesis according to the present invention.
Figure 13:
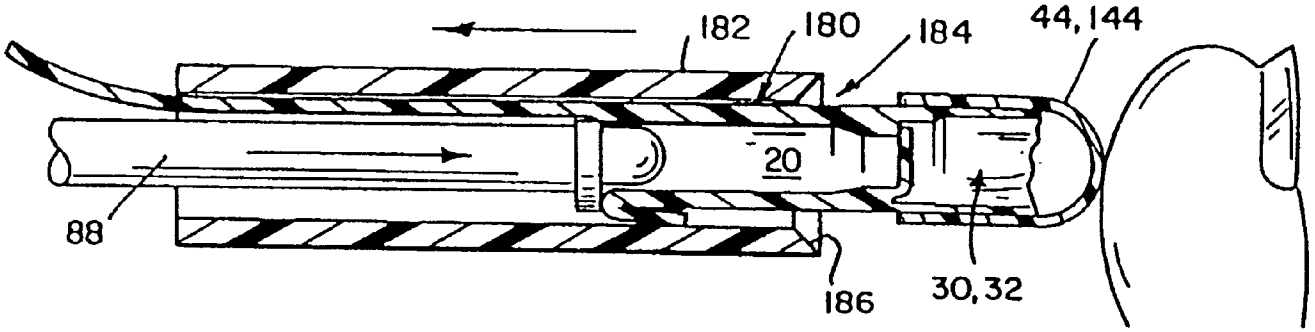

FIGS. 12–13 illustrate steps of an alternative method to that described in connection with FIGS. 8–10 for the loading of a flange 30 or 32 into a retainer 44 or 144, to the orientation illustrated in FIGS. 2–4, 6 and 7. In the first step in the method, illustrated in FIG. 12, the prosthesis 20 is inserted into a tube 180. The outer sidewall 182 of tube 180 again can be knurled or otherwise textured to aid in gripping of the tube 180 during the process. Once the prosthesis has reached the orientation illustrated in FIG. 12, the retainer 44 or 144 is placed inside the end 184 of the tube 180. The inside 186 of end 184 is bevelled slightly to help in folding the flange 30 or 32 and to guide retainer 44 or 144 into the end 184 of tube 180. The retainer 44 or 144 is held in the end 184 of tube 180 as prosthesis 20 is pushed out of tube 180 into retainer 44 or 144 by, for example, the clinician's forefinger while a tool 88 is pushed through the tube 180 (FIG. 13), engages the open end of prosthesis 20 and pushes prosthesis 20 out of tube 180 carrying the retainer 44 or 144 with it to retain flange 30 or 32 in its folded orientation illustrated in FIGS. 2–4, 6–7, 9 or 10. The prosthesis 20 is then ready for insertion using one of the methods described in connection with FIGS. 2–4 and 6–7.

What is claimed is:

1. In combination, a device for insertion into a puncture in a tracheoesophageal wall, the device including a cylindrical body having a longitudinal axis and a flexible first flange provided on an outside surface of the body, *the flange extending radially outward from the axis of the body and being continuous radially outward from the body to a radially outer edge of the flange,* the flange having a use orientation in which it projects generally outwardly from the outside surface of the body and an insertion orientation in which it is resiliently folded toward the axis of the body, and means for retaining the flange in its resiliently folded orientation, the retaining means being constructed of a material soluble in fluids present in the tracheoesophageal wall and an esophagus partially bounded by the tracheoesophageal wall.

2. The apparatus of claim 1 wherein the first flange is positioned adjacent a first end of the body which is [inserted] *insertable* through the puncture.

3. The apparatus of claim 2 and further comprising a second flange spaced along the body from the first flange toward a second end of the body.

4. The apparatus of claim 3 wherein the second flange is a flexible flange.

5. A method for inserting into [a puncture] *an opening* in a [tracheoesophageal] wall *in a human body* a device including a cylindrical *device* body having a longitudinal axis and a flexible flange provided on an outside surface of the *device* body and having a use orientation in which it projects generally outwardly from the outside surface of the *device* body comprising the steps of resiliently deflecting the flange toward the axis of the *device* body [and], placing over the resiliently folded flange a retainer of a material soluble in fluids present [in] *adjacent* the [tracheoesophageal] wall and [an esophagus partially bounded by the tracheoesophageal wall] *inserting the device into the opening*.

6. The method of claim 5 *wherein the wall has a first side and a second side,* and further comprising the step of pushing the *device* body, resiliently folded flange first, *from the first side* into the [puncture] *opening* so that the resiliently folded flange lies on [an esophageal] *the second* side of the [tracheoesophageal] wall.

7. [The method of claim 5] *A method for inserting into an opening in a wall in a human body a device including a cylindrical device body having a longitudinal axis and a flexible flange provided on an outside surface of the device body and having a use orientation in which it projects generally outwardly from the outside surface of the device body comprising the steps of resiliently deflecting the flange toward the axis of the device body and placing over the resiliently folded flange a retainer of a material soluble in fluids present adjacent the wall, the wall having a first side and a second side,* and further comprising the step of pulling the device body, resiliently folded flange first, *from the second side* into the [puncture to] *opening so* that the resiliently folded flange lies on [a tracheal] *the first* side of the [tracheoesophageal] wall.

8. [The method of claim 5 wherein] *A method for inserting into an opening in a wall in a human body a device including a cylindrical device body having a longitudinal axis and a flexible flange provided on an outside surface of the device body and having a use orientation in which it projects generally outwardly from the outside surface of the device body comprising the steps of resiliently deflecting the flange toward the axis of the device body and placing over the resiliently folded flange a retainer of a material soluble in fluids present adjacent the wall,* the steps of resiliently deflecting the flange toward the axis of the *device* body and placing over the resiliently folded flange a retainer [comprise] *comprising* the steps of inserting the *device* body in a first direction into an opening of an instrument having a cross section slightly larger than a cross section of the *device* body transverse to its longitudinal axis far enough that contact with a wall of the opening of the instrument collapses the flange, placing the retainer over the collapsed flange and pushing the *device* body in a second direction opposite the first out of the opening.

9. The method of claim 8 *wherein the wall has a first side and a second side,* and further comprising the step of pushing the *device* body, resiliently folded flange first, *from the first side* into the [puncture] *opening* so that the resiliently folded flange lies on the [esophageal] *second* side of the [tracheoesophageal] wall.

10. The method of claim 8 *wherein the wall has a first side and a second side,* and further comprising the step of pulling the *device* body, resiliently folded flange first, *from the second side* into the [puncture] *opening* so that the resiliently folded flange lies on [a tracheal] *the first* side of the [tracheoesophageal] wall.

[11. In combination, a device for insertion into a puncture in a tracheoesophageal wall, the device including a cylindrical body and a flexible first flange provided on an outside surface of the body, the flange having a use orientation in which it projects generally outwardly from the outside surface of the body and an insertion orientation in which it is resiliently folded toward the axis of the body, and means for retaining the flange in its resiliently folded orientation, the retaining means being removable to permit deployment of the flange to its use orientation.]

[12. The apparatus of claim 11 wherein the first flange is positioned adjacent a first end of the body which is inserted through the puncture.]

[13. The apparatus of claim 12 and further comprising a second flange spaced along the body from the first flange toward a second end of the body.]

[14. The apparatus of claim 13 wherein the second flange is a flexible flange.]

15. A method for inserting into a puncture in a tracheoesophageal wall a device including a cylindrical *device* body having a longitudinal axis and a flexible flange provided on an outside surface of the *device* body and having a use orientation in which it projects generally outwardly from the outside surface of the *device* body comprising the steps of resiliently deflecting the flange toward the axis of the *device* body, placing over the resiliently folded flange a retainer for retaining the flange in a folded non-use orientation, inserting the device with the retainer in place into the puncture, and removing the retainer to permit deployment of the flange to its use orientation.

16. The method of claim 15 *wherein the wall has a first tracheal side and a second esophageal side, and* the step of inserting the device with the retainer in place into the puncture comprises the step of pushing the *device* body, resiliently folded flange first, into the puncture so that the resiliently folded flange lies on [an esophageal] *the second* side of the [tracheoesophageal] wall.

17. [The method of claim 15 wherein] *A method for inserting into an opening in a wall of a human body a device including a cylindrical device body having a longitudinal axis and a flexible flange provided on an outside surface of*

*the device body and having a use orientation in which it projects generally outwardly from the outside surface of the device body comprising the steps of resiliently deflecting the flange toward the axis of the device body, placing over the resiliently folded flange a retainer for retaining the flange in a folded non-use orientation, inserting the device with the retainer in place into the opening, and removing the retainer to permit deployment of the flange to its use orientation, the wall having a first side and a second side,* the step of inserting the device with the retainer in place into the [puncture comprises] *opening comprising* the step of pulling the *device* body, resiliently folded flange first, into the [puncture] *opening* so that the resiliently folded flange lies on [a tracheal] *the first* side of the [tracheoesophageal] wall.

18. [The method of claim 15 wherein] *A method for inserting into an opening in a wall of a human body a device including a cylindrical device body having a longitudinal axis and a flexible flange provided on an outside surface of the device body and having a use orientation in which it projects generally outwardly from the outside surface of the device body comprising the steps of resiliently deflecting the flange toward the axis of the device body, placing over the resiliently folded flange a retainer for retaining the flange in a folded non-use orientation, inserting the device with the retainer in place into the opening, and removing the retainer to permit deployment of the flange to its use orientation,* the steps of resiliently deflecting the flange toward the axis of the *device* body and placing over the resiliently folded flange a retainer [comprise] *comprising* the steps of inserting the *device* body in a first direction into an opening of an instrument having a cross section slightly larger than a cross section of the *device* body transverse to its longitudinal axis far enough that contact with a wall of the opening of [an] *the* instrument collapses the flange, placing the retainer over the collapsed flange and pushing the *device* body in a second direction opposite the first out of the opening.

19. The method of claim 18 *wherein the wall has a first side and a second side,* and further comprising the step of pushing the *device* body, resiliently folded flange first, into the [puncture] *opening* so that the resiliently folded flange lies on [an esophageal] *the second* side of the [tracheoesophageal] wall.

20. The method of claim 18 *wherein the wall has a first side and a second side,* and further comprising the step of pulling the *device* body, resiliently folded flange first, into the [puncture] *opening* so that the resiliently folded flange lies on [a tracheal] *the first* side of the [tracheoesophageal] wall.

* * * * *